United States Patent [19]
Bae et al.

[11] Patent Number: 5,354,264
[45] Date of Patent: Oct. 11, 1994

[54] GAS PRESSURE DRIVEN INFUSION SYSTEM BY HYDROGEL ELECTROLYSIS

[75] Inventors: You H. Bae; Ick C. Kwon, both of Salt Lake City, Utah

[73] Assignee: Insutech, Inc., Salt Lake City, Utah

[21] Appl. No.: 18,937

[22] Filed: Feb. 17, 1993

Related U.S. Application Data

[63] Continuation-in-part of Ser. No. 783,634, Oct. 24, 1991, abandoned.

[51] Int. Cl.$^5$ ............................................. A61M 1/30
[52] U.S. Cl. ..................................... 604/21; 604/49; 604/51; 604/145; 604/66
[58] Field of Search ............... 604/20, 21, 49–51, 604/131, 140, 145, 65, 66; 222/394, 399; 169/60, 61, 71, 78

[56] References Cited

U.S. PATENT DOCUMENTS

| | | | |
|---|---|---|---|
| 2,036,739 | 4/1936 | Arnold | 222/394 |
| 2,445,477 | 7/1948 | Folkman | 604/51 |
| 3,022,785 | 2/1962 | Crockford et al. | 604/145 |
| 4,472,260 | 9/1984 | Neefe | 204/278 |
| 4,892,778 | 1/1990 | Theeuwes et al. | 428/218 |
| 5,002,055 | 3/1991 | Merki et al. | 128/635 |
| 5,062,834 | 11/1991 | Gross et al. | 604/143 |
| 5,116,312 | 5/1992 | Blankenship et al. | 604/66 |
| 5,125,894 | 6/1992 | Phipps et al. | 604/20 |

FOREIGN PATENT DOCUMENTS 385916 6/1989 European Pat. Off. .

*Primary Examiner*—C. Fred Rosenbaum
*Assistant Examiner*—Michael Rafa
*Attorney, Agent, or Firm*—Thorpe, North & Western

[57] ABSTRACT

A drug delivery device is described which utilizes gas pressure from free oxygen and hydrogen derived from the electrolysis of water at the electrodes in negatively charged polymeric hydrogels by electro-osmosis. The gas pressure forces the infusion of the drugs through appropriate means into the body. The rate of electrolysis which produces the oxygen and hydrogen is controlled by an electric current. Therefore the rate of drug delivery can be predetermined and precisely controlled. The current is activated and controlled by an electronic timer or a biomedical control system. The negatively charged hydrogel polymers have mechanical strength and rigidity and allow water to flow through the polymer network toward the cathode ensuring a continuous water supply to the electrodes inside the hydrogel system by electro-osmosis. The hydrogels may be recharged (reswollen) with water or simply replaced. Because the containment of water within the hydrogel structure is not position dependent, gravity plays no part in the gel location within the gas generation unit as in prior art units. Therefore, the contact between the electrodes and water for purposes of electrolysis is position independent.

40 Claims, 7 Drawing Sheets

GAS PRESSURE DRIVEN INFUSION SYSTEM BY HYDROGEL ELECTROLYSIS

This application is a continuation-in-part of copending application Ser. No. 07/783,634 filed Oct. 24, 1991, now abandoned.

BACKGROUND OF THE INVENTION

This invention relates to a system for the administration of drugs and/or biologically active materials by continuous intervenous infusion, utilizing gas pressure produced by the electrolysis of water in hydrogels. More particularly, this invention relates to a delivery device which utilizes gas pressure from free oxygen and hydrogen derived from the electrolysis of water in solid hydrogels providing strength and rigidity. The gas pressure forces the infusion of the drugs and/or biologically active materials through appropriate means into the body. The rate of electrolysis of water from within the hydrogel framework which produces the gases (oxygen and hydrogen) is controlled by an electric current. This current is supplied by a battery or is activated and controlled by an electronic timer or a biomedical control system which reacts to stimuli related to bodily functions, such as temperature, pH, muscle contractions, electroencephalography, or electrocardiography, and/or a combination of the above.

DESCRIPTION OF PRIOR ART

There have been many approaches to meet the problems of regulating the delivery of drugs and or biologically active materials (hereinafter collectively referred to as "drugs") in the place and at the proper dose to achieve the desired regulatory effect. Some of these systems depend on the utilization of physical or chemical stimuli which are a result of changes in the biological systems. These changes are usually of an external nature to the drug delivery system. These mechanisms respond to such stimuli or signals which include protein binding, hydrogel expanding or swelling, polymer erosion, membrane reorganization, solubility change, energy conversion, supply of activation energy for permeation, physical property changes of the materials that comprise the system, or phase transition phenomena, and the like. Examples are presented in J. Heller, *Chemically self-regulated drug delivery systems, J. Control. Rel.*, 8, 111–125 (1988) and J. Kost (ed.), *Pulsed and Self-Regulated Drug Delivery CRC Press. Inc, Boca Raton, Fla.*, 1990.

Other delivery systems currently available utilize gravity flow and other electrically driven mechanical pumps (peristaltic or syringe pumps) attached to syringes or intervenous tubing which infuse the drugs into the body. In addition, elastomeric balloons can also be utilized as the contraction force in E. Bruerar et al., Continuous sc infusion of narcotics using a portable disposable device in patients with advanced cancer, *Cancer Treatment Report*, 71, 635–637 (1987) for the portable infusion systems. These systems require large, complicated supports along with electronic or mechanical pumps which restrict their portability for ambulatory patients in hospitals or at home. Moreover, these systems have constant infusion rates which cannot be regulated in a time-released pattern required by some drugs, such as anti-cancer agents.

Gross et al., European Patent Application 0 385 915, published Sep. 5, 1990 describes a container including a displacable partition to define a first expansible-contractible chamber on one side for receiving the liquid to be dispensed, and a second expansible-contractible chamber on the opposite side for receiving an electrolytic cell. The electrolytic cell has electrodes and an electrolyte capable of generating, upon the energization of the electrodes, a gas under pressure to displace the displacable partition and to force the liquid out from the first chamber in accordance with the rate of energization of the electrodes. The electrolyte used is stated to include saline solution, other polar solutions or liquid gels, generating hydrogen, oxygen, nitrogen or carbon dioxide. Since the gas generated from the electrolyte can be nitrogen, carbon dioxide, hydrogen or oxygen, it stands to reason that the electrolyte is not limited to water. Moreover, electrolysis of a saline solution would also yield chlorine gas and perhaps other toxic materials. When used in liquid form the Gross et al. device is limited in operation to certain positions which insure contact between the electrodes and the liquid electrolyte. When contact is broken, i.e. by elevating an arm or other limb into which the device is inserted and/or attached, gas generation would cease thus severely limiting the usefulness of the device as a mobile or ambulatory drug delivery system. It is also evident from the teachings of Gross et al. that, when the electrolyte is a gel, it is meant to be a thickened or viscous form of the electrolyte because it is stated that it is the gel which produces the gas which in turn drives a piston to expel the fluid being dispensed.

OBJECTS AND BRIEF SUMMARY OF THE INVENTION

It is an object of this invention to produce a drug delivery system driven by a gas generation unit which utilizes water swollen hydrogels having a polymeric structure providing strength and rigidity wherein the water within the hydrogels can be electrolyzed into oxygen and hydrogen gases to produce the propulsion means for the infusion of drugs.

A still further object of this invention is to provide a water swollen negatively charged polymeric hydrogel system, which allows electric current and water to flow through the polymeric hydrogel network by electro-osmosis to the electrodes resulting in electrolysis of water, to produce oxygen and hydrogen gases.

Another object of this invention is to produce a simple and disposable means of infusion in which the infusion rate for the drugs can be controlled by an electric current.

Yet another object is to provide a compact infusion unit which is controlled by electrical current supplied by lightweight, leak proof batteries and regulated by means such as an electronic timer, biomedical control means or microprocessor control.

An additional object of this invention is to construct a simple, disposable propulsion means which is capable of delivering drugs in a timed pattern that can be attached or adopted to already existing infusion vehicles.

A further additional object of this invention is to create a simple and disposable infusion unit which can be employed in portable programmable infusion systems.

A still further additional object of this invention is to provide a delivery system for drugs which is activated by a biomedical control system that reacts to stimuli related to bodily functions, such as temperature, pH, muscle contractions, electroencephalography, or electrocardiography and/or combinations of the above.

These and other objects may be obtained by means of a simple infusion system which is composed of a gas generation unit and a non-expandable fluid container divided into a gas compartment and a drug delivery reservoir by a fluid tight septum. The septum may be in the form of a flexible diaphragm or a slidable piston which allows for change in volume in either the gas chamber or drug delivery reservoir. The gas compartment is in communication with the gas delivery unit to receive the oxygen and hydrogen generated therein and the drug delivery reservoir is in communication with means to convey the liquid drug to an injection site in the body of the recipient. The gas generation unit may be contiguous with the gas compartment portion of the fluid container so as to form an extension thereof or be connected to the gas compartment by tubing or other means to convey the gases generated in the gas generation unit to the gas compartment of the fluid container.

When the fluid container is an infusion bag or similar device having a non-expandable but pliable or non-rigid housing, the septum dividing the compartments will be a flexible diaphragm, membrane or similar means. When the fluid container is a rigid housing, such as a cylindrical syringe, the septum will be a piston or similar structure which frictionally, but snugly, engages the interior walls of the syringe chamber and slides in response to the pressure of the expanding electrolytic gases to expel drug solution from the drug solution reservoir.

The gas generation unit contains an anode and a cathode inserted into the water swollen negatively charged polymeric hydrogel structure. Oxygen and hydrogen are produced at these electrodes when an electric current is applied. The current may be supplied by a power source such as a battery or conventional AC or DC power lines. The power source may be regulated by or attached to an external control unit that is activated by an electronic timer, biomedical control unit or any other form controlled by a microprocessor or any such other similar means. For example, a biomedical control unit may be used which reacts to changes in bodily functions such as, temperature, pH, muscle contractions, electroencephalography, or electrocardiography, an/or any of the above in combination to energize the electrodes by producing an electric current that varies in intensity according to the strength of the stimuli. This current intensity is controlled either by voltage or by variation in the current density. The control unit may be attached to the external ends of the electrodes by socket means or any other suitable electrical connection. The anode and cathode pass into the polymeric hydrogel structure and can extend through the generation unit structure at any suitable point provided they are sealed at the place they pass through the structure so as not to permit the leakage of oxygen and hydrogen therefrom. Depending on what type of delivery is desired for a particular drug, the electrical current can be precisely controlled in such a way that the drug can be timed or constant or a combination of both and the pressure exerted by the oxygen and hydrogen gases can be pulsating or constant or a combination of both.

This drug delivery system can also be constructed so that the gas generator unit can be attached, such as by threaded or clamping means rendered gas tight by an appropriate gasket (such as an O-ring) to the gas compartment of the fluid container. This construction provides a method of reusing the gas generator system.

Further, the gas generation unit can be constructed such that the polymeric hydrogel can be removed for reswelling or replaced.

The functionality of the present system is made possible through the use of a solid water swellable polymeric hydrogel network having negative charges along the polymer backbone or fixed within the polymer network. This system allows electroconductivity to occur even when using pure water as the electrolyte. Pure water itself does not have electric conductivity compared to the saline solution taught in the Gross et al. EPO publication referenced above. However, in the present situation, electrical current can be conducted along the negative charges of the polymer backbone. This simple phenomena allows water electrolysis around the electrodes to generate hydrogen and oxygen gas only, free of chlorine or other gases which might be present in the case of saline or other solutions containing electrolyte ions.

The functioning of the invention is made possible by means of two principals governing the flow of water within the solid hydrogel network and the production of gases at the electrodes. First, the external electric current initiated by activating the flow of electricity through the electrodes implanted in the polymeric hydrogel structure causes electrolysis of the water within the hydrogel around the electrodes generating $O_2$ gas and hydrogen [$H^+$] ions at the positive electrode (anode), and $H_2$ gas and hydroxide [$OH^-$] ions at the negative electrode (cathode). Second, water supply to the electrodes within the hydrogel network is continuous through electro-osmosis (caused by an electric field in the gel) which forces water to flow inside the solid polymeric hydrogel structure from the anode side to the cathode side. Electro-osmosis is caused by the presence of a double layer around the negatively charged polymer strands. The diffuse or mobile part of the double layer is positively charged. This positive charge moves to the negative electrode and the water solvating or surrounding the positive charges must therefore flow with the positive charges thus assuring a constant water supply at the cathode.

Electro-osmosis occurs only when there are fixed (not mobile) charges on the surface of the water swollen polymeric hydrogel network. These simultaneous electric current and field effects cannot be obtained from electrolyte solutions or gelled liquids having mobile electrolytes as taught in the Gross et al. EPO patent application, supra.

When an electric current is applied to the solid polymeric water swollen hydrogels, as described herein, the gases travel along the electrodes passing through the hydrogel with the simultaneous release of oxygen at the anode and hydrogen at the cathode as more particularly shown in the drawings and following description of the invention.

BRIEF DESCRIPTION OF THE DRAWINGS

FIG. 7 is similar to FIG. 6.

DETAILED DESCRIPTION OF THE DRAWINGS AND THE INVENTION

Figure 1:
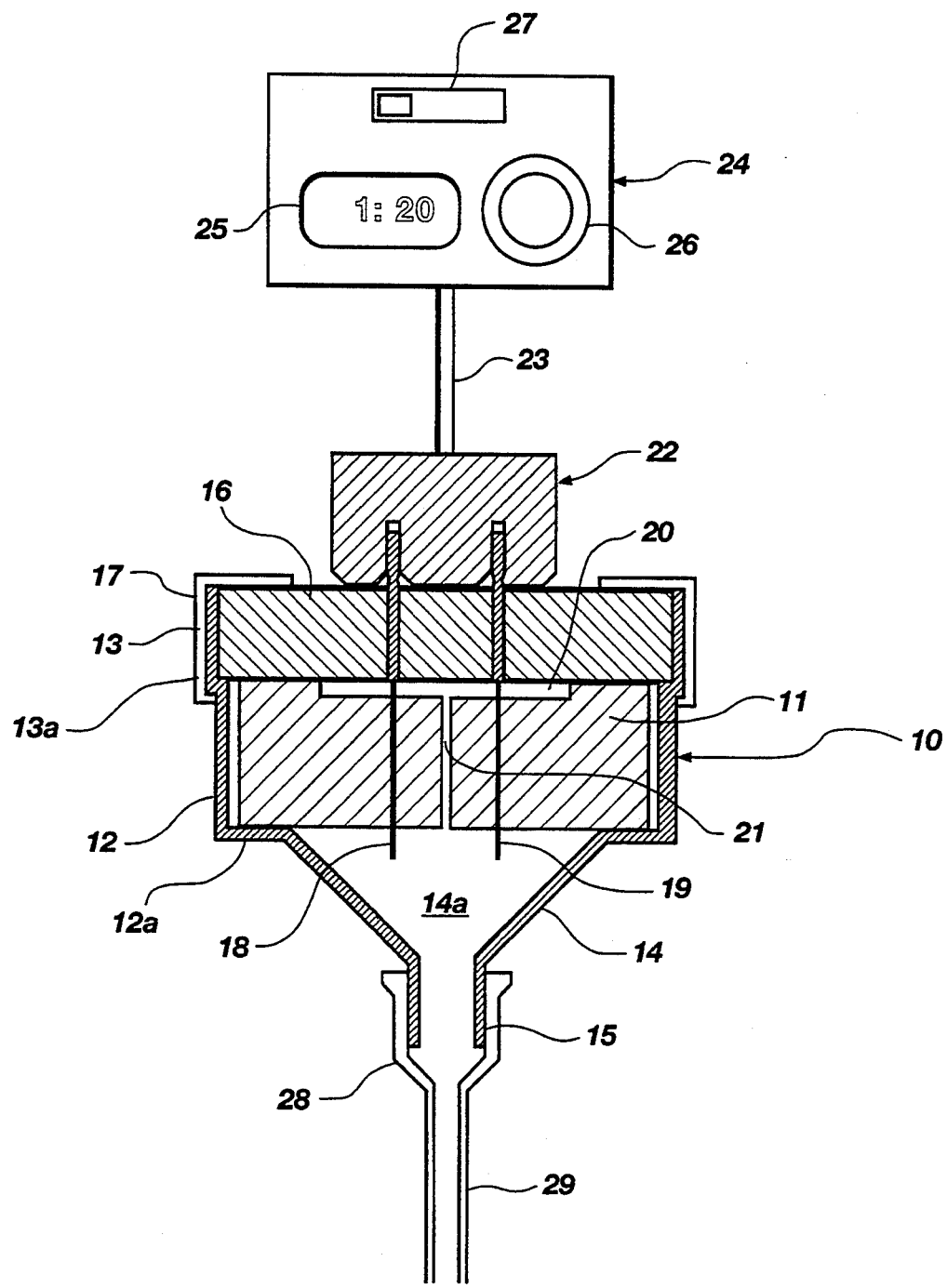
FIG. 1 shows a structural example of one embodiment of a gas generation unit in a longitudinal cross sectional view containing a negatively charged, water swollen hydrogel polymeric network and also having connected thereto an electronic controller.

FIG. 1 shows, in longitudinal cross section, a structural example of a gas generation unit 10 containing a negatively charged, water swollen hydrogel polymeric network 11. The specific structure shown is exemplary and modifications in shape and size may be readily made by one skilled in the art to provide functional equivalents. The generation unit 10 is preferably cylindrical but may be any other suitable shape. For purposes of description the gas generation unit is described as if held in a vertical position. However, this is relative as the unit may function in any position. Proceeding from top to bottom there is shown a wall portion 13 which defines a space for holding a cylindrical plug 16 through which electrodes 18 and 19 axially extend. The lower portion of wall portion 13 merges or blends into a hydrogel wall portion 12 of smaller diameter thereby forming a flange 13a upon which the outer perimeter of the plug 16 rests. Hydrogel wall portion 12 similarly defines a space for holding the hydrogel 11 (shown in FIG. 2 as being in the form of a cylindrical disk). The lower portion of wall 12 juts inwardly at a 90° angle forming a floor 12a upon which the outer perimeter of the hydrogel disk 11 rests. Floor 12a then merges or blends into an inwardly and downwardly sloping wall 14 defining a conical gas collection area 14a under the solid hydrogel disk 11. The lower portion of the housing of the gas generation unit is a hollow connection tube 15 contiguous with and extending downwardly from the wall 14. A female connector 28 at the end of a gas conduit 29 frictionally engages the outer surface of tube 15 for passage of the oxygen and hydrogen generated in unit 10.

The plug 16 is held in place by a holder 17 overlapping the upper perimeter of the plug and held in place against wall 13 by any suitable means. For example, a lower lip on plug holder 17 may snap under the lower end of wall 13. Alternatively, a friction fit or threaded engagement between the inner side of holder 17 and the outer side of wall 13 may suffice. Other means such as gluing the plug holder to the outer side of wall 13 may also be used.

Electrodes 18 and 19 extend axially through the plug 16 and into or through the hydrogel 11.

Figure 2A:
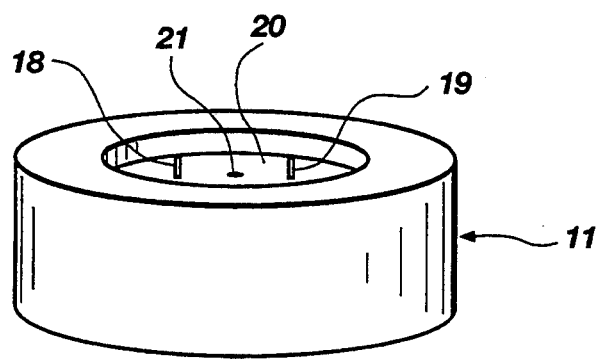
FIG. 2 illustrates the hydrogel component of the gas generation unit with FIG. 2a showing a three dimensional view of the polymeric hydrogel, FIG. 2b showing a cross sectional view and FIG. 2c showing a top view.
Figure 2B:
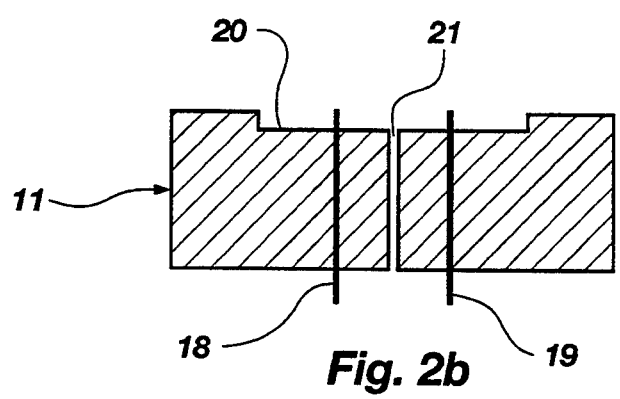
Figure 2C:
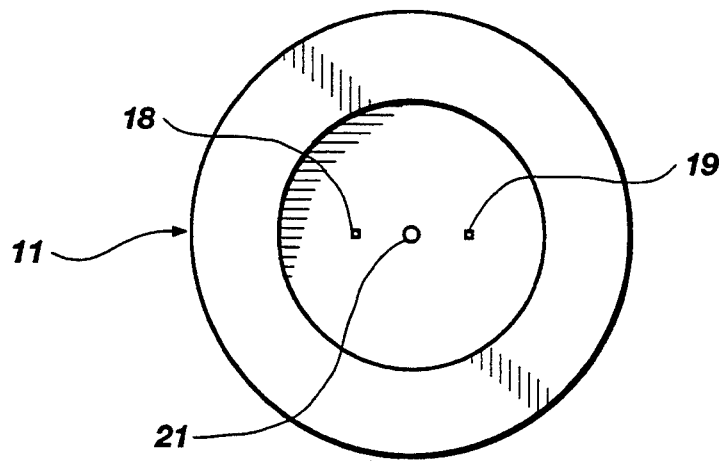

The hydrogel is better illustrated in FIGS. 2a, 2b and 2c. FIG. 2a is a three dimensional view of a hydrogel disk 11. An depression in the upper portion of hydrogel 11 forms a gas diffusion basin 20 which communicates with the gas collection area 14a below the hydrogel by means of a conduit 21 passing axially through the center of the hydrogel as shown in FIG. 1 and FIG. 2b. Therefore, the basin 20, conduit 21 and collection area 14a are in fluid communication with each other. Thus, any gas which forms at the electrodes and passes upwardly into basin 20 will migrate through conduit 21 to the collection area 14a.

Electrodes 18 and 19 pass axially through the hydrogel 11 as shown in FIG. 1 and FIGS. 2a, 2b and 2c. The electrodes, as shown in FIG. 1, may be a continuous electrode extending from above and through plug 16 and into and through hydrogel 11. In the alternative, the electrodes extending through the hydrogel 11 may frictionally fit at the upper ends thereof, through a male/female type coupling, into the lower end of electrodes embedded in and extending above the plug 16. In other words, the plug may be reused over and over and the disposable hydrogel replaced as needed without the necessity of replacing the entire electrode structure.

Means to energize and control the flow of electricity to the electrodes is generally indicated by a controller (including a microprocessor and/or biomedical control unit) 24 connected via line 23 to a socket 22 into which the electrodes 18 and 19 are plugged. Controller 24 contains the power supply and controls for regulating the energization of the electrodes 18 and 19. For example, controller 24 either houses a battery (not shown) or may be connected to an external AC or DC power supply as is appropriate. A control circuit in the controller, manipulated by an external knob 26 may regulate the flow of electricity. An on-off switch 27 may be used to turn the power supply on or off. A timer 25 or other elements commonly governed by a microprocessor may be housed within the controller to allow energization of the electrodes by any variety of conditions and/or stimuli for any selected period of time. Monitored stimuli for actuating a microprocessor may be those related to bodily functions, such as temperature, pH, muscle contractions, electroencephalography, or electrocardiography, and/or a combination of the above.

A crucial element in the proper functioning of the gas generation unit 10 lies in the makeup or construction of the solid negatively charged polymeric hydrogel and the flow of water within the gel structure. For proper operation, the electrodes 18 and 19 must always be in contact with the negatively charged polymer gel and water. This insures position-independent, solid contact between electrodes and the water within the polymeric hydrogel thereby producing gases at a constant rate regardless of the position or direction of the gas generation unit.

For this reason, the solid polymeric hydrogels must be synthesized from negatively charged polymer networks along polymer chains or from neutral polymer networks having entrapped therein linear polymers synthesized from negatively charged monomers or natural polymers.

The negatively charged polymer networks are preferably acidic polymer networks composed of synthetic, semi-synthetic, or natural monomers that contain carboxyl acid groups and/or sulfonic acid groups, singly or in combination and are inclusive of the sodium and potassium salts thereof. Examples of the synthetic acid monomers that can be utilized to form the hydrogel polymer are: allyl sulfonic acid, styrene sulfonic acid, vinyl sulfonic acid, vinyl benzene sulfonic acid, 2-acrylamido-2-methylpropane sulfonic acid, acrylic acid, methacrylic acid, allylacetic acid, 2-allylphenoxy acetic acid, 2-pentenoic acid, 2-acetoamidoacrylic acid, maleic acid, maleamic acid, 2-vinyl propionic acid, senecionic acid and their corresponding sodium and potassium salts. The crosslinked natural or modified polymer networks can be composed of acid group containing polymerized natural substances that will absorb water, such as dextran sulfate gels, protein gels, heparin gels, or a combination of such gels.

Neutral polymer networks having entrapped therein linear polymers may be synthesized from any of the above listed monomers or natural polymers.

All of these negatively charged solid hydrogel polymers have mechanical strength and rigidity and allow water to flow through the polymer network toward the cathode ensuring a continuous water supply to the electrodes inside the hydrogel system by electro-osmosis. They are versatile in that they may be recharged (reswollen) with water or simply replaced. Because the containment of water within the hydrogel structure is not position dependent, gravity plays no part in the gel location within the gas generation unit as in prior art units. Therefore, the contact between the electrodes and water for purposes of electrolysis is position independent. Because the flow of electrical current occurs along the negatively charged polymer and is not dependent upon ions within the water it is possible to use pure water to swell the hydrogel and still generate hydrogen and oxygen at the electrodes. As alluded to above, the phenomenon of electro-osmosis within a solid electrolyte system functions with water moving from the anode (+ electrode) side to the cathode (− electrode) side with the current flow if the media between the electrodes is a negatively charged polyelectrolyte. And, although water is consumed by electrolysis at the electrodes, the water is supplied continuously to the electrodes by the water flow inside the gel.

The walls of gas generator unit 10, including the plug retainer 17, may be constructed of rigid materials such as glass, metals, ceramics, and/or plastics such as polyethylene, polypropylene, polycarbonates, polystyrene, or other plastics that are rigid and impermeable to gases. The plug element 16 is made from materials that are non-conducting and sufficiently compressible to retain the electrodes in a fluid tight relationship. Examples of these materials would be a natural or synthetic rubber. If desired a semi-flexible rubber such as soft silicone rubber, neoprene, and the like could also be used. The electrodes 18 and 19 are composed of non-sacrificial materials which conduct electric current and are not decomposed by the electrolysis reaction, for example gold, silver, copper, platinum and/or any of the foregoing metal coated electrodes. The connector 28 and tubing 29 may be composed of any suitable flexible, nonporous material such as plasticized polyvinylchloride, polyurethane, polyethylene, polypropylene, silicone rubber, etc.

Figure 3:
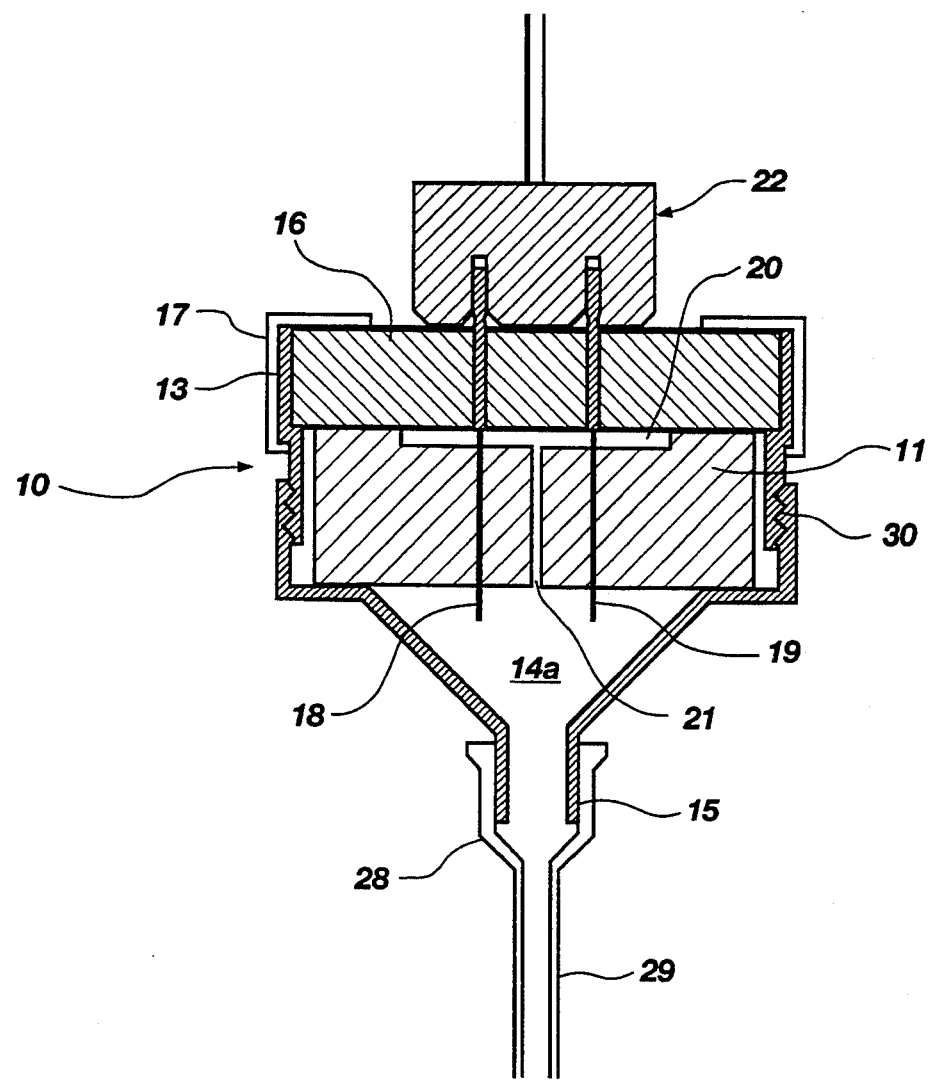
FIG. 3 is a longitudinal cross sectional view of a second embodiment of a gas generation unit similar to FIG. 1 of wherein the hydrogel housing is threaded for ready replacement of the polymeric hydrogel component.

FIG. 3 illustrates a gas delivery unit 10 which is similar in all respects to that shown in FIG. 1 except that the housing is of two-piece construction connectable at hydrogel wall portion 13 by threads 30. This allows the housing to be opened and hydrogel 11 to be readily removed for reswelling with water or to be replaced.

Figure 4:
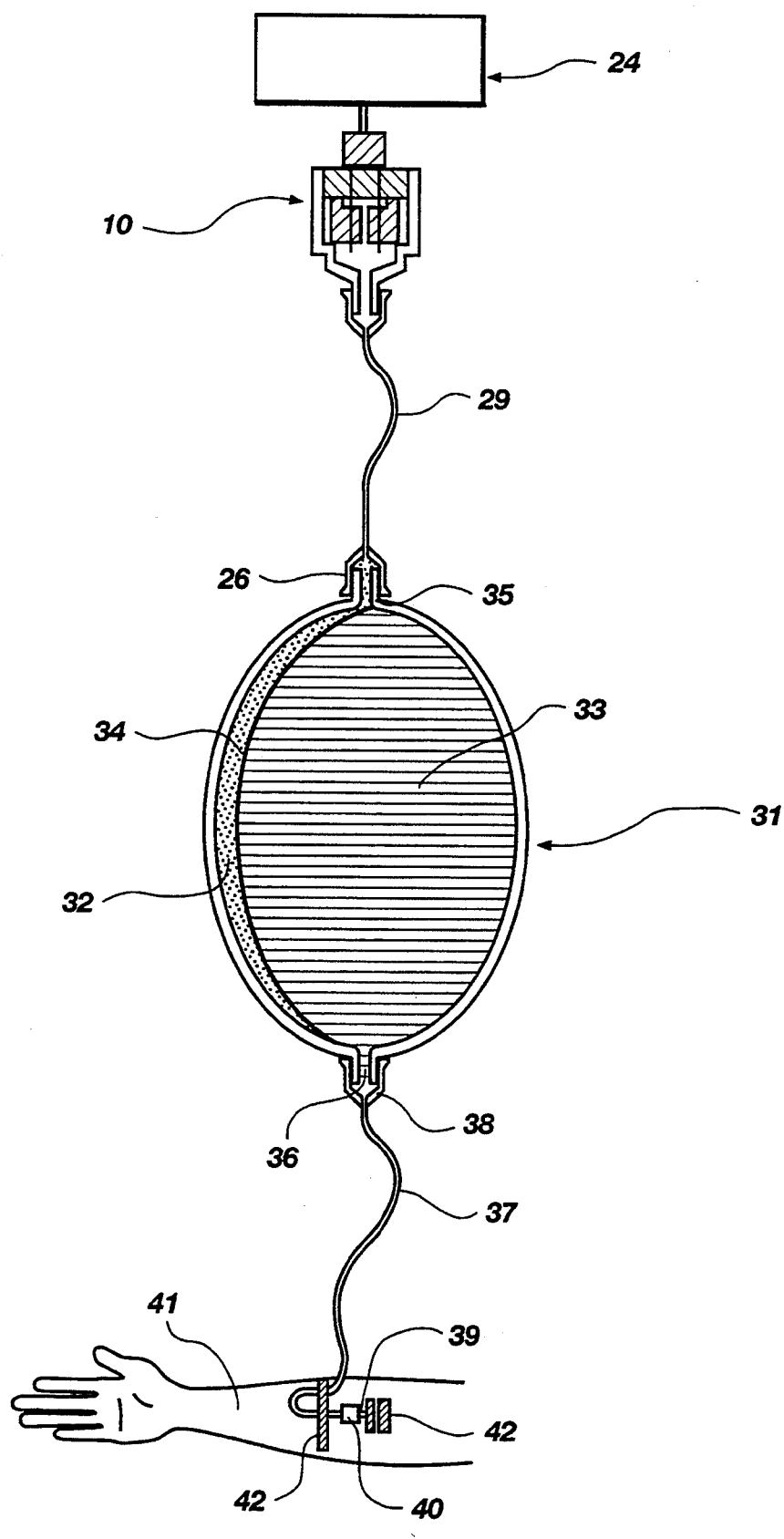
FIG. 4 shows a two-piece infusion unit consisting of the gas generation unit and a two compartment drug fluid container unit connected to a patient. The fluid container unit is divided into two expansible, contractible chambers, one being a drug reservoir chamber filled with a dispensable drug solution and the other being a chamber into which gas from the gas generation unit may expand said cheers being separated by a flexible diaphragm.

FIG. 4 shows a two-piece system for drug delivery which is composed of a gas generation unit 10 and controller 24 system which are attached to a two compartment infusion container 31 by way of gas conduit 29. The gas generation unit is essentially the same as shown in FIGS. 1 and 3 except that a single wall 12 of uniform diameter (shown as portions 12 and 13 in FIG. 1 and 3) is shown and no plug holder is illustrated.

Fluid container 31 is divided into two compartments 32 and 33 by means of a flexible diaphragm 34. One compartment is an expansible/contractible gas compartment 32 into which oxygen and hydrogen gas is received from the gas generation unit 10 via conduit 29. Receiving tube or nipple 35 provides entry access for hydrogen and oxygen gases into compartment 32. A female connector 26 at the end of conduit 29 frictionally engages and surrounds the outside surface of tube 35.

Liquid reservoir 33 contains the liquid drug to be dispensed. Dispensing tube or nipple 36 provides a port for delivery of drug solution from reservoir 33 by means of catheter 37. A female connector 38 at the end of catheter 37 frictionally engages and surrounds the outside surface of tube 36. Flexible diaphragm 34 divides the interior of infusion container 31 in a fluid tight relationship such that gas compartment 32 and drug compartment 33 are separated with gas compartment communicating with the gas generation unit 10 and drug compartment 33 communicating with delivery conduit 37.

The delivery system is completed as shown in FIG. 4 by means of hypodermic needle 39 attached by a connecting joint 40 to the catheter 37 and inserted into the arm 41 or other portion of a patient and secured by tape 42 or other securing means.

For purposes of this description the oxygen and hydrogen in gas compartment 32 and the gas compartment per se are shown as being the same as is the drug solution in drug reservoir 33 and the drug compartment per se. Because of the nature of flexible diaphragm 34, the volume of the gas compartment will be that occupied by oxygen and hydrogen from gas generation unit 10 and the volume of drug solution will occupy the entire drug reservoir 33.

Figure 5:
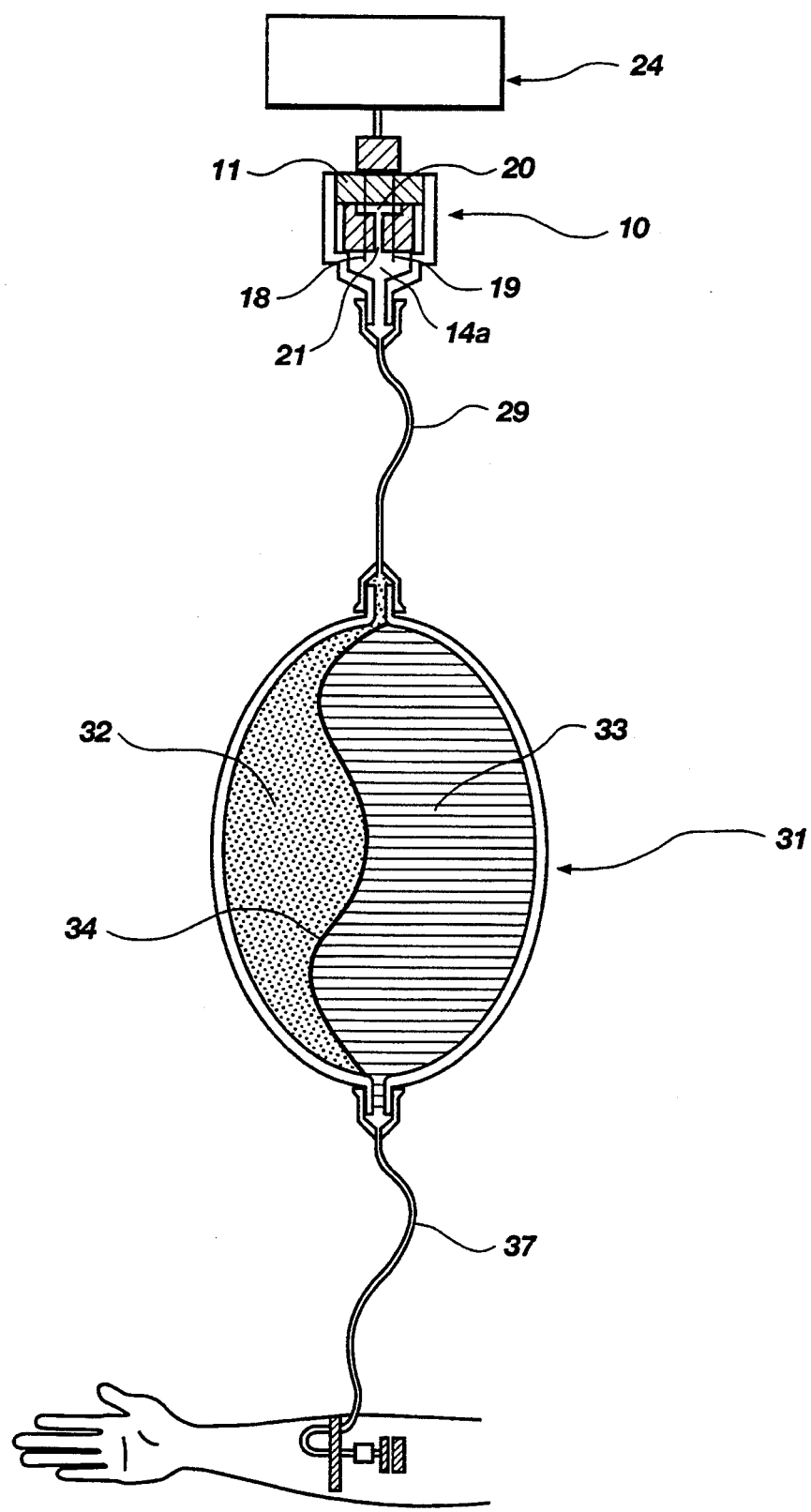
FIG. 5 is a view of the unit of FIG. 4 which illustrates the operation of a two-piece infusion unit when an electric current has been applied to generate the oxygen and hydrogen gases in the gas generation unit which then enter into and expands the gas compartment chamber by displacement of the flexible diaphragm which in turn forces the drug through an opening of the reservoir for delivery into the body.

FIG. 5 illustrates the operation of the same device described in FIG. 4 in operation as the result of electrolysis gases being generated in gas generation unit 10 and expanding into infusion unit 31. In this configuration, under the applied current to electrodes 18 and 19, as regulated by controller unit 24, the hydrolysis of the water in the negatively charged polymeric hydrogel 11 occurs and oxygen and hydrogen, are produced at the electrodes and, depending upon where they exit from the hydrogel, either pass through basin 20 and through conduit 21 to collection space 14a or are generated directly into collection space 14a. In either event, these gases pass from the gas generation unit 10, through the tubing 29 that connects the gas generator 10 with the fluid container 31. The drug solution in drug compartment 33 is displaced by these gases as they expand into gas compartment 32. The pressure exerted by the expanding gases in compartment 32 displaces flexible diaphragm 34 exerting pressure against drug solution in reservoir 33 which then forces the drug solution through catheter 37 for delivery into the body through hypodermic needle 39.

The walls or housing of fluid container 31 is made of any suitable non-expandable and impermeable materials that can be flexible or non-flexible such as glass, metals, ceramics, and/or plastics such as polyethylene, polypropylene, polycarbonates, polystyrene, polyvinylchloride or other plastics. In other words, the wall of container 31 must be non-expandable so as not to expand under the influence of the pressure of gas entering compartment 32 or upon the filling of reservoir 33 with a drug solution. However, the outer wall structure may be either flexible, deformable (pliable) or rigid depending upon the circumstances of use. The diaphragm is flexible so as to form a displacable partition or septum between compartment 32 and reservoir 33 and may be made of any suitable impermeable material such as plasticized polyvinyl chloride, polyethylene, polypropylene, polyurethane, nylon and the like. Basically, any of the materials of a flexible nature used in making the container 31 may be used. When reservoir 33 is initially filled with drug solution the fluid container volume will be essentially that occupied by reservoir 33. However, when gases enter compartment 32, the diaphragm or septum is displaced by the expanding of compartment 32 thereby forcing drug solution out of reservoir 33. When reservoir 33 has been emptied of the drug solution by means of the displacement of diaphragm 34, compartment 32 will occupy essentially all of the volume of fluid container 31.

Figure 6:
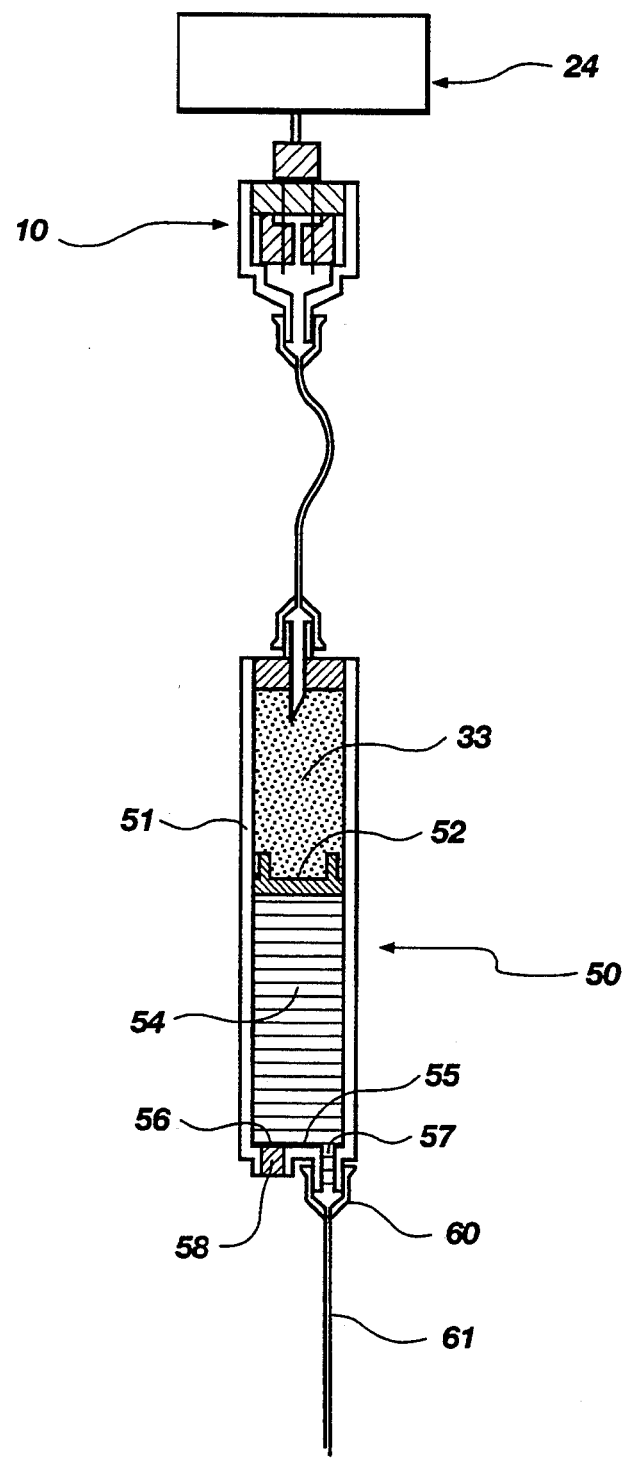
FIG. 6 shows, in longitudinal cross section, a two-piece infusion syringe consisting of the gas generation unit and a drug delivery syringe unit. The drug delivery syringe unit is divided into two expansible, contractible chambers, one being a drug reservoir chamber filled with a dispensable drug solution and the other being a chamber into which gas from the gas generation unit may expand, said chambers being separated by a piston. The piston is driven against the drug solution when the production of gases occurs in the gas generation unit and enters the gas chamber.

FIG. 6 illustrates a syringe delivery device 50 having a gas generation unit 10 and controller 24 similar to that shown in FIG. 4 wherein comparable elements in the gas generation unit 10 and controller 24 are identified by the same numerals as in FIG. 4. The syringe device or fluid container 50 is shown as having a unitary, non-expandable cylindrical wall 51 defining a barrel which is divided into two expansible contractible compartments, gas compartment 53 and drug solution reservoir 54 by a piston 52. The floor or bottom 55 of the syringe contains two ports 56 and 57. Port 56 is used for filling reservoir 54 with drug solution and is stopped with a self-sealing material 58 that will seal itself after being punctured with a needle, hollow wire or other filling means used for inserting the drug solution into reservoir 54. This filling port 56 allows the drug solution to be introduced into reservoir of the syringe device 50 at any suitable time, i.e. prior to use, as a recharge during use or for refilling following use. Any material which has self-sealing ability after puncturing by sharp needle or other filling means can be used for sealing the filling port 56. Port 57 is further defined by a nipple or tube 59 extending downwardly from floor 55. A connection joint 60 is friction fitted about nipple 59 and holds a hypodermic needle or catheter line 61.

Piston 52 frictionally engages the inner walls of barrel 51 in a fluid tight relationship and separates the hydrogen and oxygen gases, that are produced by electrolysis of the water in the negatively charged polymeric hydrogel, which enter compartment 53 from the liquid phase drug solution in reservoir 54. The piston 52 moves in response to the pressure of the gases produced by electrolysis occurring in the hydrogel. As shown in FIG. 6, the gas generation unit 10 and controller 24 are the same as described for FIGS. 1-5 except for the means by which the gases enter into gas compartment 53 from tubing 29. As shown in FIG. 6, a hollow needle or tube 62, having a blunt proximal end and a sharpened distal end, is engaged at the proximal end in female connector 36. The upper end of syringe 50 is sealed by a plug 63. The plug 63 is pierced by the sharpened end of needle 62 to permit entry of electrolysis gases from gas generation unit 10 via line 29. Plug 63 may be made from materials as used for plug 16 in FIGS. 1-5, i.e. materials that are sufficiently compressible to retain needle or tube 62 in a fluid tight relationship. Examples of these materials are natural or synthetic rubber and, if desired a semi-flexible rubber such as soft silicone rubber, neoprene could be used.

Figure 7:
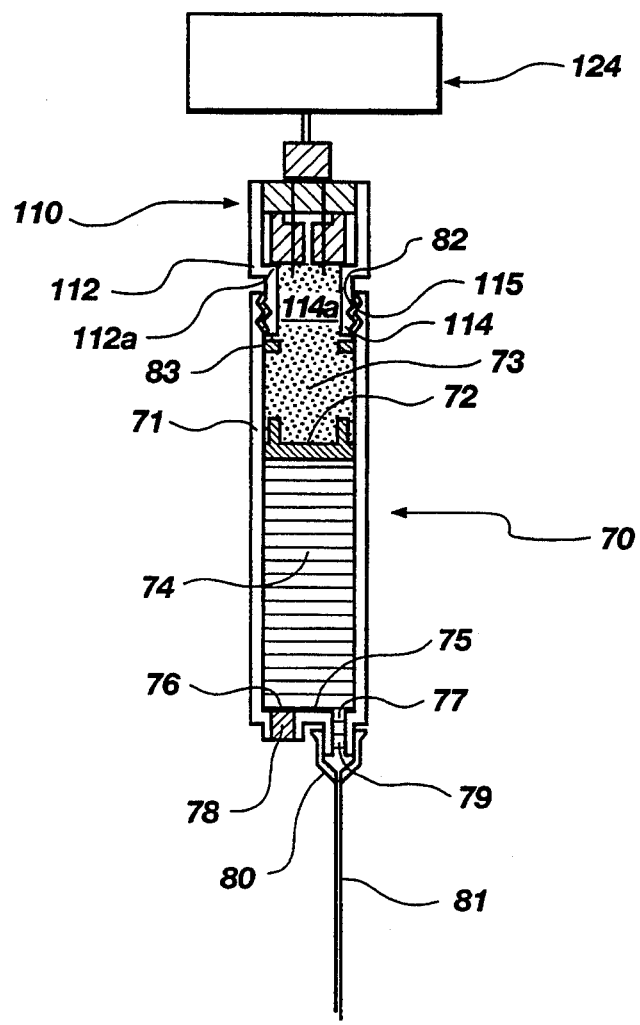
FIG. 7 shows in longitudinal cross section a one-piece infusion syringe which has the gas generation unit threaded into the barrel of the syringe as a removable top unit. Otherwise.

FIG. 7 illustrates an embodiment of a syringe type device which is unitary with the gas generation unit. There is shown a syringe 70 having a unitary, non-expandable cylindrical wall 71 defining a barrel which is divided into two expansible contractible compartments, gas compartment 73 and drug solution reservoir 74 by a piston 72. The floor or bottom 75 of the syringe contains two ports 76 and 77. Port 76 is used for filling reservoir 74 with drug solution and is stopped with a self-sealing material 78 that will seal itself after being punctured with a needle, hollow wire or other filling means used for inserting the drug solution into reservoir 74. This filling port 76 allows the drug solution to be introduced into the syringe device 70 at any suitable time, i.e. prior to use, as a recharge during use or for refilling following use. Any material which has self-sealing ability after puncturing by sharp needle or other filling means can be used for sealing the filling port 76. Port 77 is further defined by a nipple or tube 79 extending from floor 75. A connection joint 80 is friction fitted about nipple 79 and holds a needle or catheter line 81.

Piston 72 frictionally engages the inner walls of barrel 71 in a fluid tight relationship and separates the gases, which are produced by electrolysis of the water in the hydrogel and which enter compartment 73, from the liquid phase drug solution in reservoir 74. The piston 72 moves in response to the pressure of the gases produced by electrolysis occurring in the hydrogel. As shown in FIG. 7, the gas generation unit 110 and controller 124 are similar in nature and function to gas generation unit 10 and controller 24 in FIGS. 1-6. However, in this embodiment, the gas generation unit 110 is contiguous with and forms an extension of syringe 70. The upper end of syringe 70 is adapted to receive the gas generation unit 110. In that regard, the inner end portion of cylindrical wall 71 bears threads 82. Also a gasket 83 or similar stopper type means may be secured to the inner surface of wall 71 just below the threads 82 to prevent the piston 72 from moving beyond means 83 during the process of filling the syringe with drug solution and may also serve to engage and seal the bottom end of the gas generation unit as will be described.

Gas generation unit 110 has a cylindrical housing wall 112 defining a space for holding a hydrogel disk 111 and a closing plug 116. The lower portion of wall 112 merges or blends inwardly at a 90° angle forming a floor 112a upon which the outer perimeter of the hydrogel disk 111 rests. Floor 112a then merges or blends downwardly at a 90° angle forming a cylindrical wall 114 defining a cylindrical gas collection area 114a under the solid hydrogel disk 111. The outer surface of wall 114 contains threads 115. Threads 82 of wall 71 and threads 115 of wall 114 engage each other when gas generation unit 110 is secured to syringe 70 in a fluid tight relationship and the end of wall 114 may engage gasket 83 thereby providing additional means to prevent gas leakage between units 110 and syringe 70. In this embodiment, the gas compartment 73 and gas collection area 114a merge as a unitary compartment when the gas generation unit 110 is engaged in syringe 70.

In the syringe embodiments shown in FIGS. 6 and 7, the cylindrical barrel or wall 51 and 71 respectively are manufactured from rigid materials such as glass, metals, ceramics, and/or plastics such as polyethylene, polypropylene, polycarbonates, polystyrene, or other plastics.

The pistons 52 and 72 of FIGS. 6 and 7 respectively are made of rigid materials that maintain a seal against the barrel walls, as the piston (or plunger) moves in response to the gas pressure exerted by the gas generator. Examplary materials are vulcanized rubber, ground glass, and plastics such as polyethylene, polypropylene, and polytetrafluoroethylene.

The plugs 16, 63 and 116 illustrated have been defined above but should be sufficiently compressible to form a tight seal against the rigid walls of the gas generator or syringe.

The electrodes, 18, 19, 118 and 119 are composed of nonsacrificial materials which conduct electric current and are not decomposed by the electrolysis reaction, for example gold, silver, copper, platinum and/or any of the foregoing metal coated electrodes.

The invention does not lie in the specific configuration of the septum divided fluid container into which hydrogen and oxygen gases enter and through which a drug solution is administered. Neither, except as dictated by functionality, is the structure of the gas generation unit critical. Rather, it is the utilization of the negatively charged water swollen hydrogel as described above which enables the production of hydrogen and oxygen electrolysis gases at the electrodes under non-position dependent conditions to deliver precise amounts of gas under regulated conditions so as to administer exact amounts of drugs upon energization of the controller unit.

DETAILED DESCRIPTION PREFERRED EMBODIMENTS OF THE INVENTION

As can be seen from the above description of the various embodiments shown in the drawings, the invention is directed to devices that deliver drug solutions from infusion bags or syringes via catheters and/or hypodermic needles into a patient. The drug is infused into the body by pressure produced through the electrolysis of water in the negatively charged hydrogel.

The oxygen and hydrogen gases produced by the electrolysis act as a motive force to produce pressure on the drug solution by moving a septum such as piston or flexible diaphragm that produces force, at a constant rate, against the drug solution. As a result of this pressure, the drug is forced from a reservoir through appropriate means into the patient's body.

When an electric current is applied to the water swollen negatively charged hydrogel, electrolysis of the water generates two hydrogen molecules (gas) and one oxygen molecule (gas) from two molecules of the entrained water molecules (liquid). The pressure produced by the generation of these gases is proportional to the electric current that is applied to the hydrogel. When the electrical current is applied to the swollen negatively charged hydrogel, ions present in the negatively charged hydrogel network phase transfer electrons through the hydrogel allowing current to flow. The external current causes the electrolysis of the water molecules in the hydrogel surrounding the electrodes, resulting in generation of a hydrogen and oxygen gas mixture. The water supply to the electrodes is continuous through the electro-osmosis process which forces water to flow inside the charged polymeric hydrogels from the anode side to the cathode side. The electro-osmosis is caused by the presence of a double layer around the negatively charged polymer strands wherein the diffuse or mobile part of the double layer is positively charged. This positive charge moves to the negative electrode or cathode. The water solvating or surrounding the positive charges must flow with the positive charges thereby ensuring a constant and continuous water supply to the electrodes as long as there is water in the hydrogel structure.

The chemical equation for the electrolysis of water entrained in a hydrogel is as follows:

AT THE ANODE (+ ELECTRODE):  $2H_2O \longrightarrow 4H^+ + O_2 + 4e^-$

AT THE CATHODE (− ELECTRODE):  $4H_2O + 4e^- \longrightarrow 2H_2 + 4OH^-$

NET OVERALL REACTION:  $6H_2O \longrightarrow 2H_2 + O_2 + 4H^+ + 4OH^-$

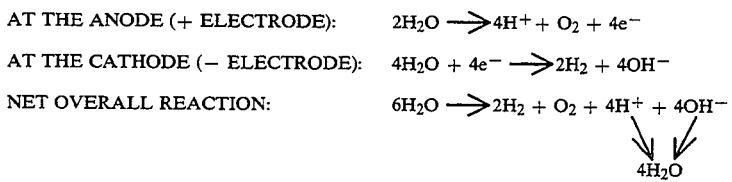

$\longrightarrow 4H_2O$

As a result, two moles of water (about 36 ml) will generate 3 moles of gas mixture (oxygen and hydrogen) which will have a volume of approximately 67.2 liters under standard conditions. Based upon the above measurements, the electrolysis of 26.7 mg water can displace 50 ml of drug solution. Moreover, the electrolysis of 5.34 mg water can replace 10 ml of liquid formulation. The electrolysis removes the above quantities of water from the hydrogel. The hydrogels can be recharged by soaking in water or replaced by fresh water swollen hydrogel.

All materials that are used in the fabrication of these drug delivery devices should be of biomedical grade and sufficiently sturdy to function for their intended use.

The delivery devices described above are particularly suitable for the delivery of drugs requiring pulsed delivery such as anti cancer drugs. These delivery devices are also useful for drugs requiring exact dosage in response to physical stimuli such as temperature, blood chemistry, rate and rhythm of heart and changes in electroactivity of the brain, more specifically antipyretics (acetylsalicylic acid, acetaminophen, etc.), antihyperglycemic agents (insulin etc.), agents for controlling cardiac erythema (atropine, digitalis etc.) and anticonvulsants (hydantoin, barbiturates etc.), for example.

The following specific examples are directed to the use of water in the drug delivery devices, however, it is intended the devices can be used with any drug solution.

EXAMPLE 1

Preparation of Hydrogel

A random, crosslinked copolymer of 2-acrylamido-2-methylpropane sulfonic acid (AMPS) and n-butylmethacrylate (BMA) was synthesized in the following manner: Dry nitrogen gas was bubbled for 20 minutes through a mixture of AMPS and BMA (total 5.39 gram, 27/73 mole ratio), dimethylforamide (5 ml), N,N'-azobisisobutyronitrile (0.1 mole % of monomer), and ethylene glycol dimethacrylate (0.8 mole % of monomer). The above mixture was polymerized in a sealed glass tube (1 cm diameter and 10 cm length) at 60° C. for 3 days. After polymerization, the polymer was removed from the glass tube by breaking the glass and was soaked in a water/acetone (50/50 v/v %) solvent mixture, the solvent was replaced daily for at least one week. The water/acetone solvent mixture in the resulting polymer was replaced with distilled water by gradually increasing the water content of the mixture until all of the acetone was removed from the polymer. The polymer was then kept in distilled water until used. The swelled hydrogel contains 70% by weight of water at a neutral pH and is slightly rigid.

EXAMPLE 2

Disposable polypropylene syringes of 3 ml capacity (0.85 cm inside diameter) were utilized in assembling a device somewhat similar to that shown in FIG. 6 but containing no piston. The plungers were removed from three syringes, leaving the hollow plastic barrels. The open end of each barrel was cut to give one barrel of 6 cm length and two barrels each having a length of 1.5 cm.

A gas generator unit was prepared from one of the 1.5 cm barrels. A fully swollen polyelectrolyte hydrogel synthesized in Example 1 was cut into a cylindrical piece of 0.8 cm diameter and 0.5 cm length and firmly inserted into one open end of one of the 1.5 cm long barrels. A disc shaped from soft silicone rubber (1 cm diameter and 0.5 cm height) was cut from a silicone sheet and inserted over the hydrogel as a sealing cap. Two platinum wire electrodes of 3 cm length were cut and inserted into the hydrogel through the silicone rubber seal. The distance between electrodes was 3 mm.

The open end of the second 1.5 cm long barrel was connected to the open end of the 6 cm long barrel by way of silicone tubing of 0.7 cm inside diameter, 0.15 cm wall thickness, and 2.5 cm length. The resulting single reservoir container, having a length of about 7.5 cm, was capped at the opposite or dispensing end of the 6 cm barrel unit and filled with water.

The gas generator and reservoir container assemblies were then interconnected at the narrowed or dispensing ends of the 1.5 cm barrels through a polyethylene tubing of 0.08 cm inside diameter and 11 cm length. The connections between the syringe barrels and tubing were made via two 18 G hypodermic needles. Finally the plastic cap at the end of the 6 cm barrel unit was replaced with a 23 G hypodermic needle.

EXAMPLE 3

When a fixed electric potential of 3 volts was applied at the platinum electrodes of the device described in Example 2, the measured current was 0.8 mA and the rate of displacement was 11.8 μl/min.

EXAMPLE 4

The relationship of infusion rate to electric current obtained with the device described in Example 2 was proportionally linear as shown in Table 1. The electric current was controlled by a potentiometer.

TABLE 1

| current (mA) | infusion rate (μl/min) |
|---|---|
| 0.77 | 10.2 |
| 0.8 | 11.8 |
| 0.85 | 11.8 |
| 1.05 | 15.2 |
| 1.1 | 14.4 |
| 1.15 | 16 |
| 1.2 | 16 |
| 1.4 | 18.5 |
| 3.4 | 48 |
| 3.5 | 49.2 |
| 7.5 | 108 |

EXAMPLE 5

A commercial 10 ml capacity glass syringe (1.55 cm inside barrel diameter, 9.5 cm barrel length) was disembled. The glass plunger end (pip part) of 1.5 cm length was cut from the plunger rod and inserted into the barrel 2 cm from the open end to function as a piston. A fully swollen polyelectrolyte hydrogel synthesized in Example 1 was cut into a cylindrical piece of 1.1 cm diameter and 1 cm length and placed in the open end of the syringe above the piston. A piece of neoprene rubber (1.7 cm diameter and 0.5 cm height) was cut shaped into a disc form and placed over the hydrogel to seal the open end of the syringe in a gas tight relationship. Two platinum wires of 3 cm length were inserted into the hydrogel through the neoprene rubber top as electrodes. The distance between electrodes was 0.5 cm.

The lower empty space (10 ml volume) was filled with distilled water. This device has the configuration to function in the manner of the syringe described in FIG. 7.

EXAMPLE 6

An electric potential of 3.50 volts was applied to the device described in Example 5. The infusion rate and current are presented in Table 2.

TABLE 2

| Time (min) | Infusion Rate (μl/min) | Current (mA) |
|---|---|---|
| 0 | 0 | |
| 5 | 65.8 | 4.5 |
| 10 | 48.6 | 2.8 |
| 15 | 41.5 | 2.7 |
| 20 | 37.9 | 2.5 |
| 25 | 36.1 | 2.3 |
| 30 | 36.1 | 2.3 |
| 35 | 36.1 | |
| 40 | 34.2 | 2.25 |
| 45 | 32.6 | 2.2 |
| 50 | 32.6 | 2.15 |
| 55 | 32.6 | |

TABLE 2-continued

| Time (min) | Infusion Rate (μl/min) | Current (mA) |
|---|---|---|
| 60 | 32.6 | 2.15 |
| 70 | 31.3 | 2.05 |
| 75 | 32.6 | |
| 80 | 32.6 | |
| 90 | 29.9 | 2.0 |
| 100 | 33.5 | |
| 110 | 33.5 | 2.2 |
| 120 | 34.4 | 2.2 |
| 130 | 32.6 | 2.1 |
| 140 | 32.6 | 2.1 |
| 150 | 32.6 | 2.1 |
| 160 | 33.6 | |
| 170 | 32.6 | 2.1 |
| 180 | 31.8 | 2.08 |
| 190 | 32.6 | 2.05 |
| 200 | 31.8 | 2.1 |
| 210 | 30.8 | 2.08 |
| 220 | 31.8 | |
| 230 | 32.6 | 2.1 |
| 240 | 34.4 | 2.08 |
| 250 | 30.8 | 2.05 |
| 260 | 31.7 | |
| 270 | 31.6 | 2.05 |
| 280 | 30.7 | 2.05 |
| 290 | 30.8 | 2.08 |
| 295 | 32.4 | 2.05 |
| 300 | 0 | |

EXAMPLE 7

A disposable polypropylene syringe of 3 ml capacity (0.85 cm inside diameter) was utilized in assembling a device similar in operation to that shown in FIG. 7 and having a rubber stopper at the open end. A rubber plunger tip was separated from the plunger rod and inserted, as a piston, into the barrel to give a space of 1.4 cm from the open end. Two holes of 0.06 cm diameter were drilled in the barrel for the electrodes. The locations of the holes were 1 cm and 0.7 cm apart respectively from the open end. The polymer hydrogel synthesized in Example 1 was cut into a disc 1.2 cm in diameter and 0.8 cm in length. The hydrogel was then dried in air for 12 hours. The diameter of the partially dried hydrogel was smaller than 0.85 cm. (the inside diameter of the barrel). This gel was then shaped by cutting off two pieces (0.4 cm from top and 0.15 cm from the side) to form gas passageways. The shaped gel was placed in the barrel and immersed in water for 12 hours. Prior to removal from the water the hydrogel was swollen and firmly inserted into the top of the barrel. A rubber stopper was inserted into the open end of the barrel over the hydrogel. Two platinum wire electrodes were inserted into the hydrogel through the holes in the barrel. A silicone sealant was applied around the electrodes and cured for 12 hours to prevent any leakage of gases (oxygen and hydrogen). The empty space below the piston was filled with distilled water.

EXAMPLE 8

An electric potential of 3 volts was applied to the device described in example 7. The average current was 2.2 mA and pumping rate was 13.2 μl/min.

While the invention has been described and illustrated with reference to certain preferred embodiments thereof, those skilled in the art will appreciate that various modifications, changes, omissions, and substitutions can be made without departing from the spirit of the invention. It is intended, therefore, that the invention be limited only by the scope of the following claims.

We claim:

1. A gas driven drug delivery device for dispensing a liquid drug at a predetermined rate, which comprises
    (a) a gas generation unit for producing oxygen and hydrogen gases by the electrolysis of water comprising a housing having affixed therein a solid water swollen negatively charged polymeric hydrogel possessing strength and rigidity, electrodes inserted into said water swollen negatively charged hydrogel and extending outwardly of said housing and means attached to said electrodes outwardly of said housing for applying an electric current to said electrodes said electrodes being positioned in said hydrogel such that oxygen and hydrogen produced will migrate out of said hydrogel along said electrodes;
    (b) a non-expandable fluid container comprising a variable volume gas compartment and a variable volume drug delivery reservoir said compartment and reservoir being separated by a fluid tight septum the position of which determines the volume of said gas compartment and drug delivery reservoir, said gas compartment being in sealed fluid communication with said gas generation unit for receiving oxygen and hydrogen produced at said electrodes under pressure and said drug delivery reservoir having an outlet passageway; and
    (c) delivery means communicating with said outlet passageway in said drug delivery reservoir for receiving displaced drug solution from said reservoir and directing said solution into the body of a patient.

2. A gas driven drug delivery device according to claim 1 wherein the negatively charged polymeric hydrogel comprises an acidic polymer network composed of synthetic, semi-synthetic, or natural monomers that contain carboxylic or sulfonic acid groups and the sodium and potassium salts thereof.

3. A gas driven drug delivery device according to claim 2 wherein the hydrogel is an acidic polymer network composed of monomers that contain sulfonic acid groups and the sodium and potassium salts thereof.

4. A gas driven drug delivery device according to claim 3 wherein said monomers are members selected from the group consisting of allyl sulfonic acid, styrene sulfonic acid, vinyl sulfonic acid, vinyl benzene sulfonic acid, 2-acrylamido-2-methylpropane sulfonic acid and the sodium and potassium salts thereof.

5. A gas driven drug delivery device according to claim 2 wherein the hydrogel is an acidic polymer network composed of monomers that contain carboxylic acid groups and the sodium and potassium salts thereof.

6. A gas driven drug delivery device according to claim 5 wherein said monomers are members selected from the group consisting of acrylic acid, methacrylic acid, allylacetic acid, 2-allylphenoxy acetic acid, 2-pentenoic acid, 2-acetoamidoacrylic acid, maleic acid, maleamic acid, 2-vinyl propionic acid, senecionic acid and the sodium and potassium salts thereof.

7. A gas driven drug delivery device according to claim 2 wherein the hydrogel is a natural polymer network composed of dextran sulfate gels, protein gels, heparin gels, and combinations thereof.

8. A gas driven drug delivery device according to claim 1 wherein said gas generation unit and said non-expandable fluid container are separate units, said gas generation unit having an outlet passageway in said housing and said gas compartment having an inlet passageway, said passageways being interconnected in a fluid tight relationship by conduit means for conveying oxygen and hydrogen produced as said electrodes to said gas compartment under pressure.

9. A gas driven drug delivery device according to claim 8 wherein said fluid tight septum separating said gas compartment from said drug delivery reservoir is a diaphragm.

10. A gas driven drug delivery device according to claim 9 wherein said fluid container is constructed of non-expandable, pliable material.

11. A gas driven drug delivery device according to claim 8 wherein said fluid container is constructed of rigid materials providing a gas compartment and liquid drug reservoir of uniform diameter and wherein said fluid tight septum separating said gas compartment from said drug delivery reservoir is a piston.

12. A gas driven drug delivery device according to claim 1 wherein said fluid container is constructed of rigid materials providing a gas compartment and liquid drug reservoir of uniform diameter and wherein said fluid tight septum separating said gas compartment from said drug delivery reservoir is a piston and wherein said gas generation unit and the gas compartment portion of said fluid container are directly joined to form a single contiguous unit.

13. A gas driven drug delivery device according to claim 12 wherein said gas generation unit and the gas compartment portion of said fluid container are directly joined by intermeshing means.

14. A gas driven drug delivery device according to claim 1 wherein said means for applying an electric current to said electrodes is a power supply adapted to energize the electrodes to produce oxygen and hydrogen gases at said electrodes and expand into said gas compartment with the resultant dispensing of liquid drug from said liquid drug reservoir at a predetermined rate determined by the rate of energization of said electrodes.

15. A gas driven drug delivery device according to claim 14 wherein said means for applying an electric current is a battery.

16. A gas driven drug delivery device according to claim 15 wherein the rate of energization of said electrodes is controlled by means selected from the group consisting of an electronic timer, a microprocessor, and a biomedical control unit.

17. A gas driven drug delivery device according to claim 16 wherein said means is an electronic timer.

18. A gas driven drug delivery device according to claim 16 wherein said means is a biomedical control unit which reacts to bodily functions selected from a group consisting of body temperature, pH of body fluids, muscle contractions, electroencephalography, and electrocardiography and combinations thereof.

19. A gas driven drug delivery device according to claim 2 wherein said negatively charged polymeric hydrogel is configured to allow hydrogen and oxygen gases produced at the electrodes to migrate along said electrodes out of said hydrogel and readily pass from any surface of said hydrogel in said gas generation unit to said gas compartment of said fluid container.

20. A gas driven drug delivery device according to claim 19 wherein said hydrogel is in the form of a disk having a depression in the disk surface opposite the flow of gases from said gas generation unit and an axial aperture through said disk permitting passage of such gases from said depression to said gas chamber in said fluid container.

21. A method for the controlled delivery of a drug to a patient, which comprises;
(1) providing an delivery system comprising:
  (a) a gas generation unit for producing oxygen and hydrogen gases by the electrolysis of water comprising a housing having affixed therein a solid water swollen negatively charged polymeric hydrogel possessing strength and rigidity, electrodes inserted into said water swollen negatively charged hydrogel and extending outwardly of said housing and means attached to said electrodes outwardly of said housing for applying an electric current to said electrodes said electrodes being positioned in said hydrogel such that oxygen and hydrogen produced will migrate out of said hydrogel along said electrodes;
  (b) a non-expandable fluid container comprising a variable volume gas compartment and a variable volume drug delivery reservoir said compartment and reservoir being separated by a fluid tight septum the position of which determines the volume of said gas compartment and drug delivery reservoir, said gas compartment being in sealed fluid communication with said gas generation unit for receiving oxygen and hydrogen produced at said electrodes under pressure and said drug delivery reservoir having an outlet passageway; and
  (c) delivery means communicating with said outlet passageway in said drug delivery reservoir for receiving displaced drug solution from said reservoir and directing said solution into the body of a patient;
(2) inserting said delivery means into a delivery site in said patient;
(3) activating said means for applying said electric current to said electrodes causing an electric current to flow between said electrodes and through said negatively charged polymeric hydrogel resulting in the electrolysis of water in said hydrogel producing oxygen and hydrogen electrolysis gases which migrate out of said hydrogel along said electrodes and expand;
(4) directing said expanding oxygen and hydrogen gases from said gas generation unit into said gas compartment of said fluid container whereby the increase in pressure resulting from said gases causes said gas compartment to increase in volume, displacing said septum and causing drug solution to be expelled from said drug solution reservoir, through said delivery means into said patient at a rate predetermined by the degree of energization of the electrodes.

22. A method according to claim 21 wherein the negatively charged polymeric hydrogel comprises an acidic polymer network composed of synthetic, semisynthetic, or natural monomers that contain carboxylic or sulfonic acid groups and the sodium and potassium salts thereof.

23. A method according to claim 22 wherein the hydrogel is an acidic polymer network composed of monomers that contain sulfonic acid groups and the sodium and potassium salts thereof.

24. A method according to claim 23 wherein said monomers are members selected from the group consisting of allyl sulfonic acid, styrene sulfonic acid, vinyl sulfonic acid, vinyl benzene sulfonic acid, 2-acrylamido-2-methylpropane sulfonic acid and the sodium and potassium salts thereof.

25. A method according to claim 22 wherein the hydrogel is an acidic polymer network composed of monomers that contain carboxylic acid groups and the sodium and potassium salts thereof.

26. A method according to claim 25 wherein said monomers are members selected from the group consisting of acrylic acid, methacrylic acid, allylacetic acid, 2-allylphenoxy acetic acid, 2-pentenoic acid, 2-acetoamidoacrylic acid, maleic acid, maleamic acid, 2-vinyl propionic acid, senecionic acid and the sodium and potassium salts thereof.

27. A method according to claim 22 wherein the hydrogel is a natural polymer network composed of dextran sulfate gels, protein gels, heparin gels, and combinations thereof.

28. A method according to claim 21 wherein said gas generation unit and said non-expandable fluid container are separate units, said gas generation unit having an outlet passageway in said housing and said gas compartment having an inlet passageway, said passageways being interconnected in a fluid tight relationship by conduit means for conveying oxygen and hydrogen produced as said electrodes to said gas compartment under pressure.

29. A method according to claim 28 wherein said fluid tight septum separating said gas compartment from said drug delivery reservoir is a diaphragm.

30. A method according to claim 29 wherein said fluid container is constructed of non-expandable, pliable material.

31. A method according to claim 28 wherein said fluid container is constructed of rigid materials providing a gas compartment and liquid drug reservoir of uniform diameter and wherein said fluid tight septum separating said gas compartment from said drug delivery reservoir is a piston.

32. A method according to claim 21 wherein said fluid container is constructed of rigid materials providing a gas compartment and liquid drug reservoir of uniform diameter and wherein said fluid tight septum separating said gas compartment from said drug delivery reservoir is a piston and wherein said gas generation unit and the gas compartment portion of said fluid container are directly joined to form a single contiguous unit.

33. A method according to claim 32 wherein said gas generation unit and the gas compartment portion of said fluid container are directly joined by intermeshing means.

34. A method according to claim 21 wherein said means for applying an electric current to said electrodes is a power supply adapted to energize the electrodes to produce oxygen and hydrogen gases at said electrodes and expand into said gas compartment with the resultant dispensing of liquid drug from said liquid drug reservoir at a predetermined rate determined by the rate of energization of said electrodes.

35. A method according to claim 34 wherein said means for applying an electric current is a battery.

36. A method according to claim 35 wherein the rate of energization of said electrodes is controlled by means selected from the group consisting of an electronic timer, a microprocessor, and a biomedical control unit.

37. A method according to claim 36 wherein the means is an electronic timer.

38. A method according to claim 36 wherein said means is a biomedical control unit which reacts to bodily functions selected from a group consisting of body temperature, pH of body fluids, muscle contractions , electroencephalography, and electrocardiography and coordinations thereof.

39. (once amended) A method according to claim 22 wherein said negatively charged polymeric hydrogel is configured to allow hydrogen and oxygen gases produced at the electrodes to migrate along said electrodes out of said hydrogel and readily pass from any surface of said hydrogel in said gas generation unit to said gas compartment of said fluid container.

40. A method according to claim 39 wherein said hydrogel is in the form of a disk having a depression in the disk surface opposite the flow of gases from said gas generation unit and an axial aperture through said disk permitting passage of such gases from said depression to said gas chamber in said fluid container.

* * * * *